United States Patent [19]
Lam

[11] Patent Number: 6,071,256
[45] Date of Patent: Jun. 6, 2000

[54] DETACHABLE PADDING FOR A NECK BRACE

[76] Inventor: Beverly J. Lam, 2709 Louise Ave., Baltimore, Md. 21214

[21] Appl. No.: 09/019,020

[22] Filed: Feb. 5, 1998

[51] Int. Cl.[7] .................................................. A61F 5/00
[52] U.S. Cl. ..................................... 602/18; 128/DIG. 23
[58] Field of Search .............. 602/17, 18; 128/DIG. 23; 2/44, 45; 119/857; D24/191; 604/358, 359

[56] References Cited

U.S. PATENT DOCUMENTS

| | | | |
|---|---|---|---|
| 4,539,982 | 9/1985 | Bailly | 602/3 |
| 4,576,150 | 3/1986 | Auracher | 602/18 |
| 4,966,136 | 10/1990 | Bates | 602/18 |
| 5,342,333 | 8/1994 | Tanzer et al. | 604/359 |
| 5,437,612 | 8/1995 | Moore et al. | 602/18 |

Primary Examiner—Richard J. Apley
Assistant Examiner—Denise Pothier

[57] ABSTRACT

A new detachable padding for a neck brace for providing contoured pads that are shaped to fit the contours of a neck brace. The inventive device includes a plurality of pads mountable to the front and back portions of a neck brace. Each pad includes a liquid permeable top layer, a substantially liquid impermeable bottom layer, and a liquid absorbing inner padding layer interposed between the top layer and the bottom layer. The back surface of the bottom layer is designed for adhesively coupling to another surface, such as the inside of a neck brace.

8 Claims, 2 Drawing Sheets

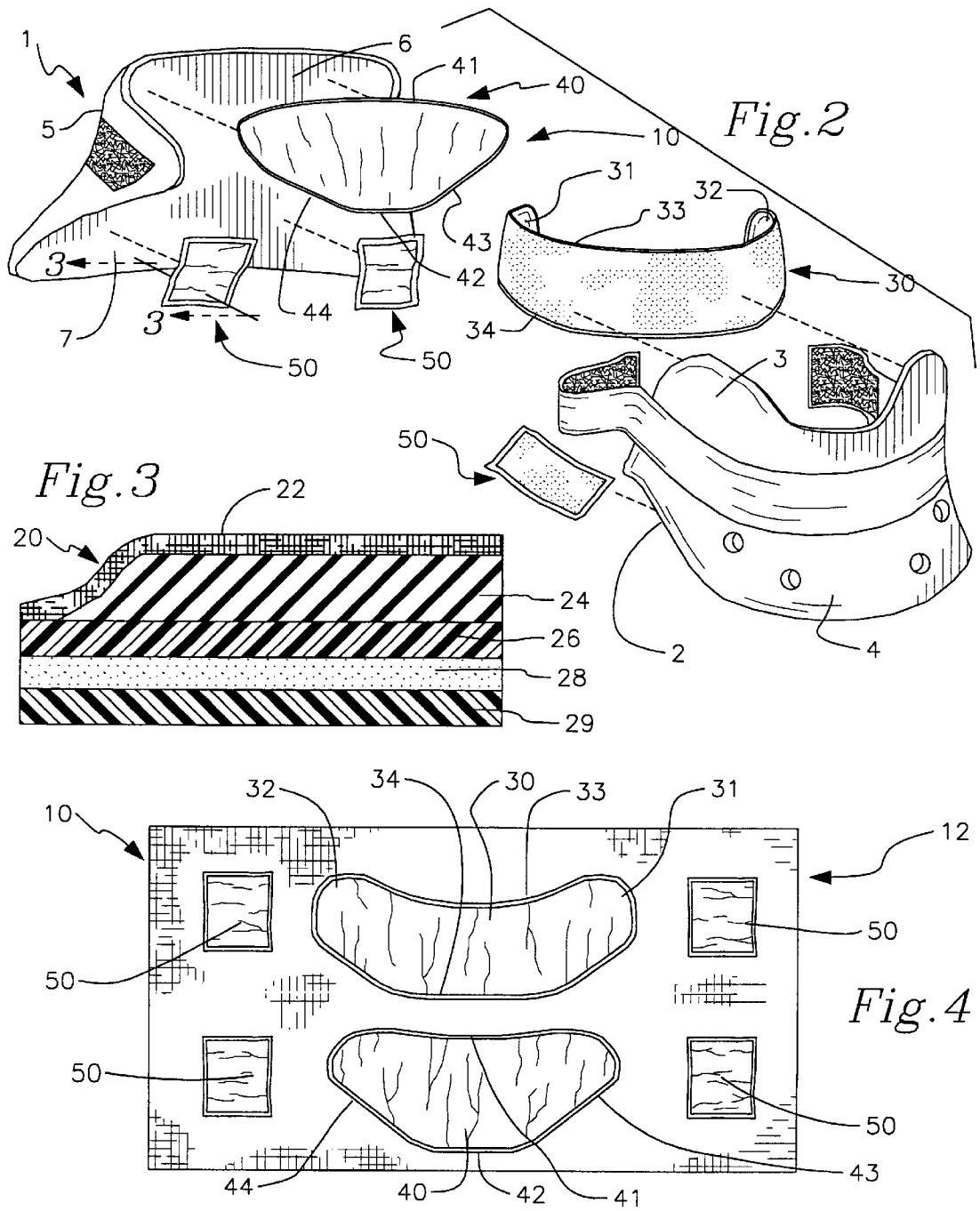

DETACHABLE PADDING FOR A NECK BRACE

BACKGROUND OF THE INVENTION

1. Field of the Invention

The present invention relates to padding for neck braces and more particularly pertains to a new detachable padding for a neck brace for providing contoured pads that are shaped to fit the contours of a neck brace.

2. Description of the Prior Art

The use of padding for neck braces is known in the prior art. More specifically, padding for neck braces heretofore devised and utilized are known to consist basically of familiar, expected and obvious structural configurations, notwithstanding the myriad of designs encompassed by the crowded prior art which have been developed for the fulfillment of countless objectives and requirements.

Known prior art padding for neck braces include U.S. Pat. No. 5,087,506; U.S. Pat. No. 5,101,846; U.S. Pat. No. Des. 307,353; U.S. Pat. No. 5,417,234; U.S. Pat. No. 5,312,386; and U.S. Pat. No. 4,678,465.

While these devices fulfill their respective, particular objectives and requirements, the aforementioned patents do not disclose a new detachable padding for a neck brace. The inventive device includes a plurality of pads mountable to the front and back portions of a neck brace. Each pad includes a liquid permeable top layer, a substantially liquid impermeable bottom layer, and a liquid absorbing inner padding layer interposed between the top layer and the bottom layer. The back surface of the bottom layer is designed for adhesively coupling to another surface, such as the inside of a neck brace.

In these respects, the detachable padding for a neck brace according to the present invention substantially departs from the conventional concepts and designs of the prior art, and in so doing provides an apparatus primarily developed for the purpose of providing contoured pads that are shaped to fit the contours of a neck brace.

SUMMARY OF THE INVENTION

In view of the foregoing disadvantages inherent in the known types of padding for neck braces now present in the prior art, the present invention provides a new detachable padding for a neck brace construction wherein the same can be utilized for providing contoured pads that are shaped to fit the contours of a neck brace.

The general purpose of the present invention, which will be described subsequently in greater detail, is to provide a new detachable padding for a neck brace apparatus and method which has many of the advantages of the padding for neck braces mentioned heretofore and many novel features that result in a new detachable padding for a neck brace which is not anticipated, rendered obvious, suggested, or even implied by any of the prior art padding for neck braces, either alone or in any combination thereof.

To attain this, the present invention generally comprises a plurality of pads mountable to the front and back portions of a neck brace. Each pad includes a liquid permeable top layer, a substantially liquid impermeable bottom layer, and a liquid absorbing inner padding layer interposed between the top layer and the bottom layer. The back surface of the bottom layer is designed for adhesively coupling to another surface, such as the inside of a neck brace.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new detachable padding for a neck brace apparatus and method which has many of the advantages of the padding for neck braces mentioned heretofore and many novel features that result in a new detachable padding for a neck brace which is not anticipated, rendered obvious, suggested, or even implied by any of the prior art padding for neck braces, either alone or in any combination thereof.

It is another object of the present invention to provide a new detachable padding for a neck brace which may be easily and efficiently manufactured and marketed.

It is a further object of the present invention to provide a new detachable padding for a neck brace which is of a durable and reliable construction.

An even further object of the present invention is to provide a new detachable padding for a neck brace which is susceptible of a low cost of manufacture with regard to both materials and labor, and which accordingly is then susceptible of low prices of sale to the consuming public, thereby making such detachable padding for a neck brace economically available to the buying public.

Still yet another object of the present invention is to provide a new detachable padding for a neck brace which provides in the apparatuses and methods of the prior art some of the advantages thereof, while simultaneously overcoming some of the disadvantages normally associated therewith.

Still another object of the present invention is to provide a new detachable padding for a neck brace for providing contoured pads that are shaped to fit the contours of a neck brace.

Yet another object of the present invention is to provide a new detachable padding for a neck brace which includes a plurality of pads mountable to the front and back portions of a neck brace. Each pad includes a liquid permeable top layer, a substantially liquid impermeable bottom layer, and a liquid absorbing inner padding layer interposed between the top layer and the bottom layer. The back surface of the bottom layer is designed for adhesively coupling to another surface, such as the inside of a neck brace.

Still yet another object of the present invention is to provide a new detachable padding for a neck brace that help eliminate the irritation and discomfort of wearing a neck brace.

Even still another object of the present invention is to provide a new detachable padding for a neck brace that absorbs body moistures such as sweat and wound secretions.

Even still another object of the present invention is to provide a new detachable padding for a neck brace that may be treated with deodorizing compounds to help reduce odors occurring from long term wearing of a neck brace.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a schematic exploded perspective view of the present invention detailing a preferred positioning of the pads on a neck brace.

FIG. 3 is a schematic cross sectional view taken from line 3—3 on FIG. 2 of the present invention showing the layers of the pads.

FIG. 4 is a schematic top side view of the pads formed on a pad sheet of the present invention.

DESCRIPTION OF THE PREFERRED EMBODIMENT

Figure 1:
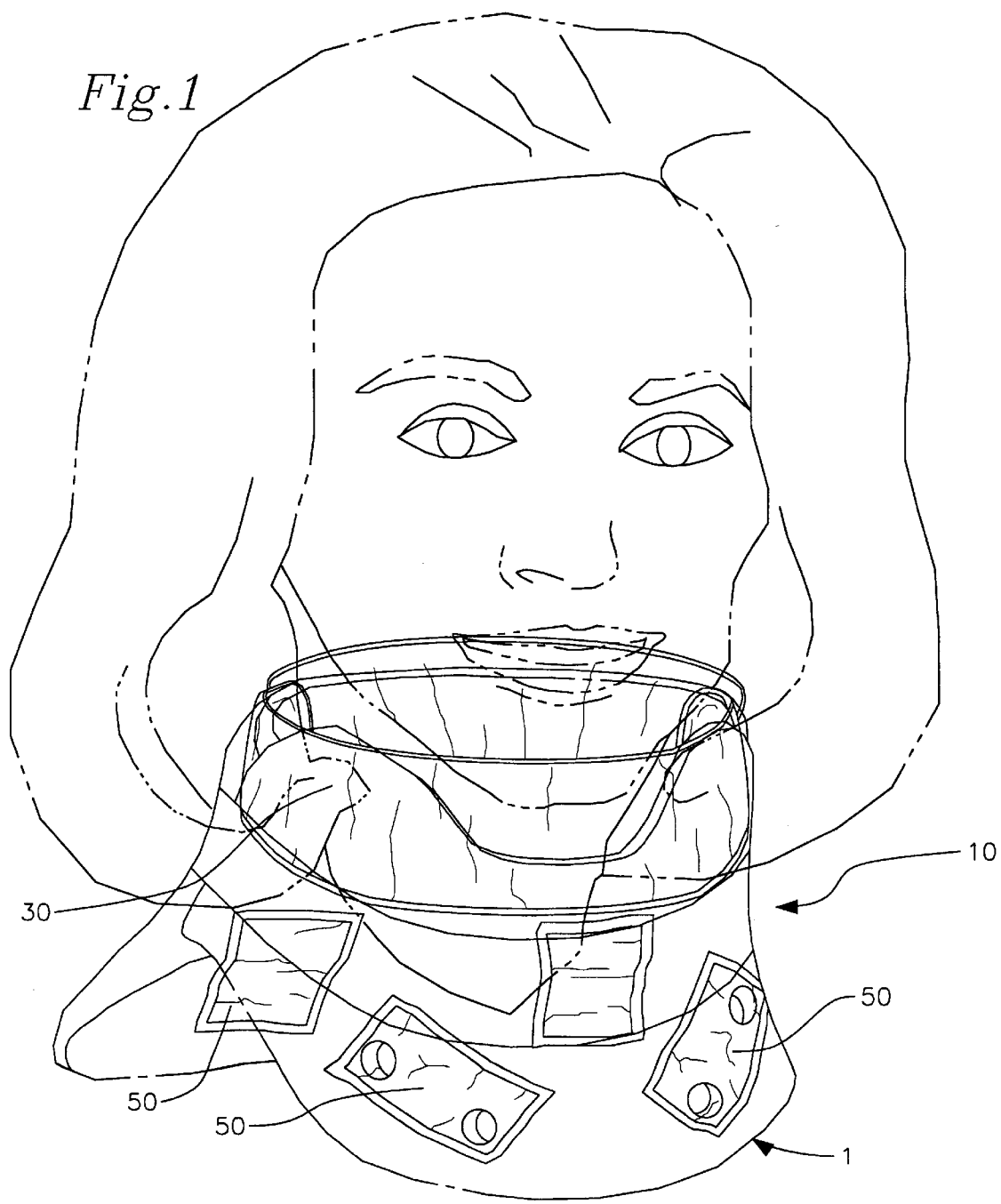
FIG. 1 is a schematic perspective view of a new detachable padding for a neck brace being worn on the neck of a user according to the present invention.

With reference now to the drawings, and in particular to FIGS. 1 through 4 thereof, a new detachable padding for a neck brace embodying the principles and concepts of the present invention and generally designated by the reference numeral 10 will be described.

The padding set 10 is designed for mounting to a typical neck brace 1 having separable front and back portions 2,5 each having a top region 3,6 and a bottom shoulder resting region 4,7. As best illustrated in FIGS. 1 through 4, the detachable padding for a neck brace 10 generally comprises a plurality of pads 20 mountable to the front and back portions 2,5 of a neck brace 1. Each pad 20 includes a liquid permeable top layer 22, a substantially liquid impermeable bottom layer 26, and a liquid absorbing inner padding layer 24 interposed between the top layer 22 and the bottom layer 26. The back surface of the bottom layer 26 is designed for adhesively coupling to another surface, such as the inside of a neck brace 1.

The pads 20 of the padding set 10 preferably include a front chin pad 30, a back neck pad 40, and a plurality of clavicle pads 50. As shown in FIG. 3, each pad 20 includes a liquid permeable top layer 22, a liquid absorbing inner padding layer 24, and a substantially liquid impermeable bottom layer 26. The top layer 22 abuts adjacent the skin of a wearer of a neck brace 1 when the pads 20 are mounted on the neck brace 1. The liquid permeable top layer 22 is designed for permitting fluids, such as body secretions, to pass through it. Ideally, the top layer 22 may also have medication applied to it for helping heal any wounds that may be in contact with it when a neck brace is worn.

The inner padding layer 24 is interposed between the top layer 22 and the bottom layer 26 and is designed for absorbing fluids. Preferably, the inner padding layer 24 is compressible so that neck brace 1 may be securely fitted on a wearer without defeating the support that the neck brace 1 provides to the neck of a wearer. Ideally, the inner padding layer 24 includes a deodorant for deodorizing odors from fluids absorbed by the inner padding layer 24.

Preferably, applied on the back surface of the bottom layer 26 is an adhesive 28 for permitting adhesive coupling of the back surface of the bottom layer 28 to another surface, such as a neck brace. Ideally, a removable protective cover sheet 29 substantially covers the adhesive 28 on the back surface of the bottom layer 26. The protective cover sheet 29 may be removed from the back surface of the bottom layer 26 to permit adhesion by the adhesive 28 of the back surface of the bottom layer 26 to a surface.

With reference to FIGS. 2 and 4, the front chin pad 30 has a generally elongate arcuate shape comprising a pair of opposite lateral lobes 31,32 and a pair of spaced apart upper and lower edges 33,34 extending between the lobes 31,32. The front chin pad 30 is mountable to the front portion 2 of a neck brace 1 such that the lateral lobes 31,32 extend towards the top region 3 of the front portion 2 of the neck brace 1 so that the lateral lobes 31,32, as shown in FIG. 1, may be fitted on either side of the chin and below the jaw of a wearer of the neck brace.

The back neck pad 40 has a generally trapezoidal shape comprising upper and lower edges 41,42 connected by a pair of lateral side edges 43,44 that taper towards the lower edge 42 of the back neck pad 40. The back neck pad 40 is mountable to the back portion 5 of a neck brace 1 such that the upper edge 41 of the back neck pad 40 extends towards the top region 6 of the back portion 5 of the neck brace 1. This permits fitting of the back neck pad 40 to the upper neck and lower back of the skull of a wearer of the neck brace 1.

The clavicle pads 50 are generally rectangular in shape and are mountable to the front and back portions 2,5 of a neck brace 1 towards the bottom shoulder resting regions 4,7 of the neck brace 1. This allows the clavicle pads 50 to be fitted to protect the collar bone and other portions of the shoulder of a wearer on which the neck brace 1 rests upon.

Optionally, with reference to FIG. 4, the plurality of pads 20 may be formed on a pad sheet constructed having the top layer 22, the inner padding layer 24, the bottom layer 26 with the adhesive 28 and the cover sheet 29 on it. The pads 20 are then removable from the pad sheet 12 by either cutting them out or by perforations provided through the pad sheet 12.

In use, the pads 20 are attached to their respective portion of the neck brace 1 by first removing the cover sheet 29 from the adhesive 28 and then adhesively coupling the bottom layer 26 to the neck brace 1. The pads 20 also may be used to provide protection and an absorption means to other types of braces.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A padding set for providing padding to the inside of a neck brace, the neck brace having front and back portions each having a top region and a bottom shoulder resting region, said padding set comprising:

a plurality of pads being mountable to the front and back portions of a neck brace;

each pad including a liquid permeable top layer, a liquid absorbing inner padding layer, and a substantially liquid impermeable bottom layer;

said inner padding layer being interposed between said top layer and said bottom layer; and said bottom layer having a back surface, said back surface of said bottom layer being for adhesively coupling to another surface;

wherein said plurality of pads includes a front chin pad, a back neck pad, and a plurality of clavicle pads;

wherein said plurality of pads are formed on a pad sheet, said pads being removable from said pad sheet said pad sheet including a liquid permeable top layer, a liquid absorbing inner padding layer, and a substantially liquid impermeable bottom layer, said bottom layer having a back surface, said back surface of said bottom layer having an adhesive thereon for permitting adhesive coupling of said back surface of said bottom layer to another surface, and a removable protective cover sheet substantially covering said adhesive on said back surface of said bottom layer.

2. The padding set of claim 1, wherein said bottom layer of each pad has a back surface, said back surface of said bottom layer having an adhesive thereon for permitting adhesive coupling of said back surface of said bottom layer to another surface.

3. The padding set of claim 2, further comprising a removable protective cover sheet substantially covering said adhesive on said back surface of said bottom layer.

4. The padding set of claim 1, wherein said inner padding layer includes a deodorant for deodorizing odors from fluids absorbed by said inner padding layer.

5. The padding set of claim 1, wherein said front chin pad has a generally elongate arcuate shape comprising a pair of opposite lateral lobes and a pair of spaced apart upper and lower edges extending between said lobes, said front chin pad being mountable to the front portion of a neck brace such that said lateral lobes extend towards the top region of the front portion of the neck brace so that said lateral lobes may be fitted on either side of the chin and below the jaw of a wearer of the neck brace.

6. The padding set of claim 1, wherein said back neck pad has a generally trapezoidal shape comprising upper and lower edges connected by a pair of lateral side edges, said side edges of said back neck pad tapering towards said lower edge of said back neck pad, said back neck pad being mountable to the back portion of a neck brace such that said upper edge of said back neck pad extends towards said top region of the back portion of the neck brace so that said back neck pad may be fitted to the upper neck and lower back of the skull of a wearer of the neck brace.

7. The padding set of claim 1, wherein said clavicle pads are generally rectangular in shape, said clavicle pads being mountable to the front and back portions of a neck brace towards the bottom shoulder resting regions of the neck brace so that the clavicle pads may be fitted to protect the collar bone and other portions of the shoulder of a wearer of a neck brace on which the neck brace rests upon.

8. A padding set for providing padding to the inside of a neck brace, the neck brace having front and back portions each having a top region and a bottom shoulder resting region, said padding set comprising:

a plurality of pads including a front chin pad, a back neck pad, and a plurality of clavicle pads;

each pad including a liquid permeable top layer, a liquid absorbing inner padding layer, and a substantially liquid impermeable bottom layer;

said inner padding layer being interposed between said top layer and said bottom layer;

said bottom layer having a back surface, said back surface of said bottom layer having an adhesive thereon for permitting adhesive coupling of said back surface of said bottom layer to another surface;

a removable protective cover sheet substantially covering said adhesive on said back surface of said bottom layer;

wherein said inner padding layer includes a deodorant for deodorizing odors from fluids absorbed by said inner padding layer;

wherein said front chin pad has a generally elongate arcuate shape comprising a pair of opposite lateral lobes and a pair of spaced apart upper and lower edges extending between said lobes, said front chin pad being mountable to the front portion of a neck brace such that said lateral lobes extend towards the top region of the front portion of the neck brace so that said lateral lobes may be fitted on either side of the chin and below the jaw of a wearer of the neck brace;

wherein said back neck pad has a generally trapezoidal shape comprising upper and lower edges connected by a pair of lateral side edges, said side edges of said back neck pad tapering towards said lower edge of said back neck pad, said back neck pad being mountable to the back portion of a neck brace such that said upper edge of said back neck pad extends towards said top region of the back portion of the neck brace so that said back neck pad may be fitted to the upper neck and lower back of the skull of a wearer of the neck brace; and said clavicle pads being generally rectangular in shape, said clavicle pads being mountable to the front and back portions of a neck brace towards the bottom shoulder resting regions of the neck brace so that the clavicle pads may be fitted to protect the collar bone and other portions of the shoulder of a wearer of a neck brace on which the neck brace rests upon.

* * * * *